(12) United States Patent
Reichow et al.

(10) Patent No.: US 8,491,119 B2
(45) Date of Patent: Jul. 23, 2013

(54) ANAGLYPHIC DEPTH PERCEPTION TRAINING OR TESTING

(75) Inventors: Alan W. Reichow, Beaverton, OR (US); Karl Citek, Beaverton, OR (US); Graham B. Erickson, Hillsboro, OR (US); Herb Yoo, Beaverton, OR (US)

(73) Assignee: Nike, Inc., Beaverton, OR (US)

( * ) Notice: Subject to any disclaimer, the term of this patent is extended or adjusted under 35 U.S.C. 154(b) by 103 days.

(21) Appl. No.: 13/214,743

(22) Filed: Aug. 22, 2011

(65) Prior Publication Data
US 2011/0304818 A1 Dec. 15, 2011

Related U.S. Application Data

(63) Continuation of application No. 12/628,347, filed on Dec. 1, 2009, now Pat. No. 8,002,408, which is a continuation-in-part of application No. 12/534,661, filed on Aug. 3, 2009, now Pat. No. 7,980,963.

(51) Int. Cl.
*A61B 3/08* (2006.01)
*A61B 3/00* (2006.01)
*G02C 7/10* (2006.01)

(52) U.S. Cl.
USPC ............................ 351/201; 351/246; 351/163

(58) Field of Classification Search
USPC ............... 351/200–246, 163, 165, 41, 44, 49, 351/158
See application file for complete search history.

(56) References Cited

U.S. PATENT DOCUMENTS

| | | | |
|---|---|---|---|
| 3,861,790 A | 1/1975 | Tamura | |
| 5,050,982 A | 9/1991 | Meissner | |
| 5,478,239 A | 12/1995 | Fuerst et al. | |
| 6,158,865 A | 12/2000 | Kreutzig | |
| 6,755,525 B2 | 6/2004 | Reichow et al. | |
| 6,811,258 B1 | 11/2004 | Grant | |
| 6,893,127 B2 | 5/2005 | Reichow | |
| 7,073,208 B2 | 7/2006 | Penque, Jr. et al. | |
| 8,197,065 B2 * | 6/2012 | Yoo et al. | ...... 351/203 |
| 2001/0048505 A1 | 12/2001 | Siliphant | |

OTHER PUBLICATIONS

Reichow, et al., "Introduction to Behavioral Optometry", Sports Vision, 1993, 75 pages, Optometric Extension Program Foundation, United States.

Ferreira, "An Overview of Research in Sports Vision; its History and an Optometric Perspective", The South African Optometrist, Dec. 2003, pp. 142-149, vol. 62, No. 4, Auckland Park, South Africa.

Coffey, et al., "Visual Performance Enhancement in Sports Optometry", Sports Vision 1995, pp. 158-177, Butterworth-Heinermann, United States.

(Continued)

*Primary Examiner* — Mohammed Hasan
(74) *Attorney, Agent, or Firm* — Shook, Hardy & Bacon L.L.P.

(57) ABSTRACT

An anaglyphic image presentation system is provided to evaluate and train a user's depth perception abilities. In embodiments, anaglyphic image target components are presented to a user on a display device. The image target components are then viewed by the user through a set of transmission filter lenses. The transmission filter lenses present and block one or more target components based on the peak wavelength transmission associated with each lens. As a result, a user perceives an anaglyphic target image that is resultant from the perceived image target components when viewed through the transmission filter lenses.

20 Claims, 12 Drawing Sheets

OTHER PUBLICATIONS

Cardall, "Contact Lenses in Sport: a General Overview", Optician, Jan. 13, 2006, pp. 22-25, vol. 231, No. 634, United States.

Rouse, et al., "A Comparison Study of Dynamic Visual Acuity Between Athletes and Nonathletes", Journal of the American Optometric Association, Dec. 1988, pp. 946-950, vol. 59, No. 12, United States.

Koenig, "Practicing Perception: Eyes Can Be Trained to be More Effective", USA Today Baseball Weekly, 1996, 3 pages, United States.

Coffey, et al., "Optometric Evaluation of the Elite Athlete," Problems in Optometry, Mar. 1990, pp. 32-59, vol. 2, No. 1, United States.

Reichow, et al., "A Comparison of Contrast Sensitivity in Elite Athletes Versus a Normal Population", American Journal of Optometry and Physiological Optics, Dec. 15, 1986, vol. 63, No. 82, United States.

Farrow, et al., "An Investigation of the Effectiveness of Bolle's Competivision Sport-Glasses on Tennis Performance", Clinical and Experimental Optometry, Jul.-Aug. 2000, pp. 226-231, vol. 83, No. 4.

Herdman, et al., "Computerized Dynamic Visual Acuity Test in the Assessment of Vestibular Deficits", The American Journal of Otology, 1998, pp. 790-796, vol. 19, No. 6, United States.

Tian, et al., "Dynamic Visual Acuity During Transient and Sinusoidal Yaw Rotation in Normal Ulilaterally Vestibulopathic Humans", Experimental Brain Research, Feb. 8, 2001, pp. 12-25, vol. 137, Springer-Verlag, United States.

Reichow, et al., "Ultraviolet and Short Wavelength Visible Light Exposure: Why Ultraviolet Protection Alone is Not Adequate", Journal of Long-Term Effects of Medical Implants, 2006, pp. 315-325, vol. 16, No. 4, Begell House, Inc., United States.

Office Action of Nov. 30, 2010: U.S. Appl. No. 12/534,661, 13 pages, Aug. 3, 2009.

\* cited by examiner

1400

| | | | | | | | |
|---|---|---|---|---|---|---|---|
| LEVEL 4 | | | | | | | CORRECT |
| LEVEL 3 | CORRECT | INCORRECT | | | CORRECT | CORRECT | |
| LEVEL 2 | | | CORRECT | CORRECT | | | |
| LEVEL 1 | | | | | | | |

*FIG. 14.*

ANAGLYPHIC DEPTH PERCEPTION TRAINING OR TESTING

CROSS-REFERENCE TO RELATED APPLICATIONS

This application is a continuation of U.S. application Ser. No. 12/628,347, filed Dec. 1, 2009 now U.S. Pat. No. 8,002,408 B2, entitled "Anaglyphic Depth Perception Training Or Testing", which is a continuation-in-part of U.S. patent application Ser. No. 12/534,661 (U.S. Pat. No. 7,980,693), entitled "Anaglyphic Depth Perception Training Or Testing, filed Aug. 3, 2009, the entirety of each is hereby incorporated by reference.

TECHNICAL FIELD

The present invention relates generally to visual training and/or testing. More particularly, the present invention relates to the training and/or evaluation of the retinal disparity sensitivity aspect of an individual's depth perception abilities as isolated from differences in the vergence amplitude aspect of an individual's depth perception abilities.

BACKGROUND OF THE INVENTION

Numerous activities, such as competitive athletics, place particularized demands upon the depth perception abilities of an individual. While anaglyphic systems to present three-dimensional images to an individual have long been known, those systems have suffered from poor optics and/or limited image filtering capabilities. Other known systems, such as LCD eyewear used in conjunction with a synchronized display device, have been expensive and cumbersome.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

The present invention offers several practical applications in the technical arts, not limited to systems and methods for testing and/or training an individual's depth perception abilities. Systems in accordance with the present invention present one or more anaglyphic images to a user on an anaglyphic image display device, and those images are then viewed by the user through a set of transmission filter lenses in order to simulate the appearance of an object(s) appearing at various depths in relation to the background of the display device. An anaglyphic image presentation system in accordance with the present invention may include an anaglyphic image display device, a set of transmission filter lenses, an input device, and a control unit. By allowing a user to perceive a plurality of displayed colored visual indicia against a background through transmission filter lenses, systems in accordance with the present invention may simulate the appearance of depth and/or three-dimensional space to the user.

An input device may receive an input from a user in response to displayed visual indicia. In exemplary embodiments, anaglyphic display of colored images on the display device comprises at least two colored indicia that are perceived through a set of transmission filter lenses. The display of the colored images acting as components of at least one anaglyphic image may be controlled using a control unit so as to match the peak wavelength emitted from each colored image to the peak wavelength transmitted through the set of transmission filter lenses, or to avoid bleed-through. For instance, when red and blue transmission filter lenses are used, the display of the anaglyphic display device may comprise at least one red indicia and at least one blue indicia, with the red indicia and the blue indicia tuned by a control unit to match the peak wavelength transmitted through the red and blue lenses, respectively. In embodiments, a red indicia may be perceived by an eye viewing through a blue transmission filter lens. When the red indicia is viewed by an eye through a blue transmission filter lens, the previous red indicia may be appear to be black (or dark) color against a bluish background. Further, when viewed by an eye through a red transmission filter lens, a red indicia may be the same or similar color and luminance as the background, and therefore may not be perceived, as the formerly red indicia may blend into the background. Likewise, a blue indicia may be perceived by the eye viewing through the red transmission filter lens, where the formerly blue indicia may appear to be a black (or dark) color against a reddish background. Further, the blue indicia may be the same or similar color and luminance as the background when viewed through the blue transmission filter lens, and therefore may not be perceived, as the formerly blue indicia may blend into the background. The matching of peak wavelength transmitted to peak wavelength emitted allows the indicia to be perceived and blocked in an alternative manner when viewed through the set of transmission filter lenses, wherein each lens is matched to the peak wavelength emitted by one set of colored indicia displayed in accordance with embodiments of the present invention. It is the ability to view indicia of only one color with one filter that forms the basis of the anaglyphic image presentation system described in embodiments of the invention.

In alternative embodiments, the matching of a peak wavelength transmitted may comprise one of a range of nearby wavelength values. One feature of the present invention is the ability to limit or eliminate color bleed-through across more than one transmission filter lens. Color bleed-through, wherein a portion of the color spectrum is visible across more than one transmission filter lens, causes the resulting anaglyphic image to appear fuzzy. By decreasing or eliminating color bleed-through, the resulting anaglyphic image perceived by a user has a high degree of clarity.

In further alternative embodiments, the peak wavelength emitted by each set of colored indicia is modified to emit at the high and low range, respectively, of the peak wavelength transmitted by each lens of the set of transmission filter lenses. As such, in embodiments, each transmission filter lens of the set of transmission filter lenses is selected to be widely separated from the other transmission filter lens (e.g., in a set of transmission filter lenses, a right lens may be selected to be "red" and a left lens may be selected to be "blue"). By altering the peak wavelength emitted by each set of colored indicia displayed, such that the wavelength perceived for each object is on the lower end of the blue range or the upper end of the red range, respectively, the resultant anaglyphic image may have less bleed-through, and may have a crisper image, than if the peak wavelength emitted by the anaglyphic image components and the peak wavelength transmitted through each transmission filter lens were exactly matched.

In alternative embodiments, anaglyphic images may be composed to give the perception of various degrees of depth through the placement of the colored indicia across different portions of the anaglyphic image display device. In particular, anaglyphic images may appear to hover, or float, in front of or behind a plane of regard. For example, a retinal disparity difference between components of a first anaglyphic image and components of a second anaglyphic image may be 12 arcseconds. Accordingly, an individual perceiving the resultant anaglyphic image may perceive the image as having 12 arcseconds of float between the first image and the second image. In this way, float is relative between images and/or between an image and a plane of regard.

In embodiments, various degrees of depth perception may be achieved by changing the distance between an image component of a first wavelength and an image component of a second wavelength. This distance may be referred to as the pixdelta. Again using the example of a blue indicia and a red indicia as components of an anaglyphic image, the orientation of a blue indicia and a red indicia to the left and right portion of a display device, respectively, would appear to be hovering in front of a background panel when viewed with a set of transmission filter lenses comprising a blue left lens and a red right lens, respectively. As the blue indicia and red indicia move farther apart (i.e., as the blue indicia moves further left and/or the red indicia moves further right), the resulting anaglyphic image would appear to hover further and further in front of the background panel (e.g., the resulting anaglyphic image would appear to come closer to the user). In this example, the pixdelta would become increasingly positive as the indicia grow further apart, where the positive connotation is due to the relative relation of the blue indicia and red indicia as consistent with the relative relation of the blue left transmission filter lens to the red right transmission filter lens.

Conversely, given the same system as described above except with the blue indicia and red indicia reversed (such that the blue indicia is presented on the right part of the display device and the red indicia is presented on the left part of the display device), the resulting anaglyphic image would appear to hover behind the background panel when viewed with a set of transmission filter lenses comprising a red right lens and a blue left lens, respectively. Similar to the results above, as the blue indicia and red indicia move farther apart (e.g., as the blue indicia moves further right and/or the red indicia moves further left), the image would appear to hover farther behind the background panel. In this example, the pixdelta would become increasingly negative as the indicia grew further apart, where the negative connotation is due to the reverse relation of the blue indicia and red indicia as being inconsistent with the relative relation of the blue left transmission filter lens to the red right transmission filter lens.

A control unit may be used to present and arrange the one or more colored indicia used as anaglyphic image components of the anaglyphic image presentation system. In one embodiment, anaglyphic image components may be presented on the anaglyphic image display device based on test instructions executed by the control unit. During the display of anaglyphic image components, the test instructions may serve to control the pixdelta between the displayed anaglyphic image components.

In operation, when training an individual's depth perception in accordance with embodiments of the present invention, the individual may be prompted to engage the input device when the first anaglyphic image presented in one area of the display device with a varying pixdelta seems to match the depth of a second anaglyphic image presented on another portion of the display device with a stationary pixdelta. Once the user has indicated that the condition has been met by inputting a response into the input device, the control unit may detect a time of the engagement and determine preciseness of the individual's response based on a comparison of the engagement time and an expected time (i.e., the time the first anaglyphic image actually encounters the same depth as the second anaglyphic image). Alternatively, assuming a constant change of depth difference in the first anaglyphic image, the degree of difference of depth between the first anaglyphic image and the second anaglyphic image when the individual enters a response into the input device may be used as a measure of the speed and accuracy of an individual's depth perception. In instances, the control unit may store other information related to training, evaluation, or user depth perception abilities.

BRIEF DESCRIPTION OF THE SEVERAL VIEWS OF THE DRAWINGS

The present invention is described in detail below with reference to the attached drawing figures, wherein:

FIG. 14 illustrates a step-training mechanism in accordance with embodiments of the present invention.

DETAILED DESCRIPTION OF THE INVENTION

Figure 1:
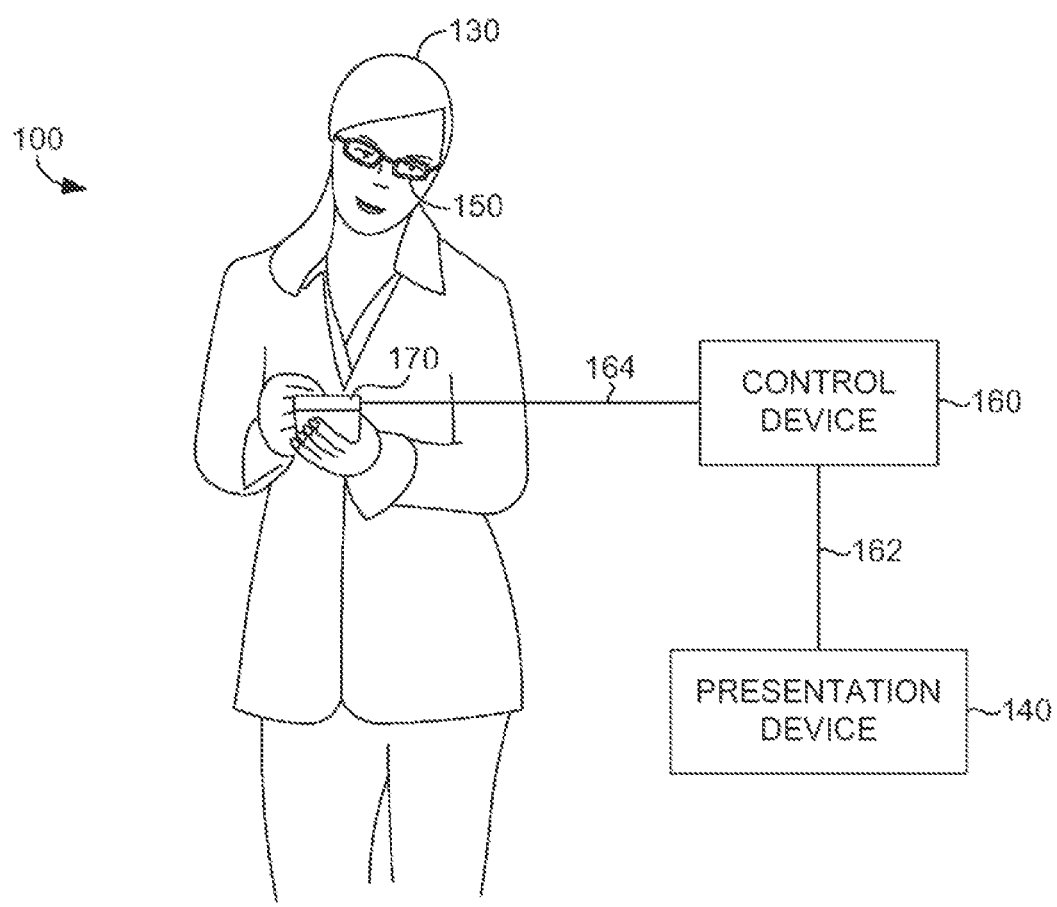
FIG. 1 illustrates an anaglyphic image presentation system in accordance with an embodiment of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

Embodiments of the invention provide an anaglyphic image presentation system for training and/or evaluating the depth perception abilities of an individual. By way of example only and not limitation, a suitable anaglyphic image presentation system may include an anaglyphic image display device that presents a plurality of perceived target images, each perceived target image associated with a left display image component and a right display image component. In particular, for a given display of a perceived anaglyphic target, a display device displays three components: a background display, a left target display component, and a right target display component, with the background, left target display component, and right target display component each comprising a set of properties. In embodiments, a set of properties associated with each type of display may include: a displayed wavelength and a displayed luminance brightness. Additionally, the anaglyphic image presentation system may diversify the area(s) of the display device that is used to display a plurality of perceived target images, where the plurality of perceived target images may comprise a plurality of target display component images. In this way, by moving the target display components across the display device of the anaglyphic image presentation system, a user may perceive a series of different targets associated with a plurality of depth perception measurements/distances. In embodiments of the invention, a perceived target display is given an appearance of depth by varying the pixdelta (i.e., the distance between the placement of indicia) between the left display image component and the right display image component. A pixdelta may comprise the raw distance, such as measured in centimeters, between two image components, or may refer to a number of pixels on the display between two image components.

The display device may also display a background that is tailored to emit a wavelength that, when viewed through a set of transmission filter lenses, is perceived as having a color that is of equal luminance between the left perceived target component and the right perceived target component when viewed through an associated transmission filter lens for each perceived target image, respectively. In an exemplary embodiment, the anaglyphic image presentation system further comprises a control unit for presenting the plurality of target display components as perceived anaglyphic images so as to create the appearance of depth of associated perceived target images, and an input device to be engaged by the individual to indicate which perceived target image(s) of a plurality of perceived target images displayed on a display device possesses the greatest appearance of depth associated with the perceived target image.

In embodiments, when training the depth perception of an individual with the anaglyphic image display device, the perceived target display components may be strategically positioned with a plurality of pixdelta properties such that the associated perceived target images may possess an appearance of depth that is perceived at the base level of the display plane, perceived at a depth in front of the display plane, or perceived at a depth behind the display plane.

Having briefly described an embodiment of the present invention, an exemplary operating environment for the present invention is described below.

Embodiments of the invention may be described in the general context of an anaglyphic display device that functions according to computer code or machine-useable instructions (e.g., test instructions), including computer-executable instructions such as program components, being executed by a computing device (e.g., control unit, input device, or recording device) or other logic-processing machine, such as a personal data assistant or other handheld device. Generally, program components including routines, programs, indicia, components, data structures, and the like, refer to code that performs particular tasks, or implement particular abstract data types. Embodiments of the present invention may be practiced in a variety of system configurations, including hand-held devices, consumer electronics, general-purpose computers, specialty computing devices, etc.

Embodiments of the depth perception training/testing system, and the anaglyphic image display device employed thereby, will now be described with reference to the accompanying drawings. The drawings and the associated descriptions are provided to illustrate embodiments of the present invention and not to limit the scope thereof. Reference in the specification to an "embodiment" is intended to indicate that a particular feature, structure, or characteristic described in connection with the embodiment is included in at least one embodiment of the invention. Further, the appearance of the phrase "in one embodiment" in various places in the specification are not necessarily all referring to the same embodiment.

Referring to the drawings in general, and initially to FIG. 1 in particular, an anaglyphic image presentation system 100 is shown, in accordance with an embodiment of the present invention. In an exemplary embodiment, the anaglyphic image presentation system 100 comprises an anaglyphic image display device 140, a set of transmission filter lenses 150, a control unit 160, and an input device 170. The anaglyphic image display device 140 may be arranged between an individual 130 being tested and the set of transmission filter lenses 150.

With reference to FIG. 1, the control unit 160 will now be discussed. Generally, the control unit 160 is configured to provide for testing and/or training of the depth perception ability of the individual 130. It will be understood and appreciated by those of ordinary skill in the art that the control unit 160 is merely an example of one suitable computing device and is not intended to suggest any limitation as to the scope of use or functionality of embodiments of the present invention. Accordingly, the control unit 160 may take the form of various types of processors that are commonly deployed in a personal computing device, a handheld device, a consumer electronic device, and the like. It should be noted, however, that embodiments of the present invention are not limited to implementation on any particular processing components.

The present invention may be used to test depth perception, such as the accuracy of depth judgment, at a wide range of distances. In embodiments, a user may be presented with two or more images at varying perceived depths and may be asked to select an image that has a small difference in depth information as compared with at least one other image. As such, the present invention may be used for depth perception testing/training with specific application to a variety of activities. For example, depth perception related to sports such as soccer, hockey, football, etc. may be tested and/or trained in accordance with long- and short-range depth aspects of the present invention. In other embodiments, depth perception related to activities such as billiards may be tested and/or trained in accordance with short-range depth aspects of the present invention.

In an exemplary embodiment, the control unit 160 is generally configured to be any type of microprocessor that is capable of executing test instructions. By way of example only and not limitation, executing test instructions may include presenting color indicia representing anaglyphic image components on an anaglyphic image display device 140. Control unit 160 may also control any additional visual characteristics, such as color, orientation, rotation, trajectory, etc. In one instance, providing anaglyphic image components may involve, but is not limited to, the following process: presenting the anaglyphic image components on the anaglyphic image display device 140, maintaining anaglyphic image components for a predetermined amount of time (e.g., millisecond to minutes), and deactivating the anaglyphic image display device 140 by returning it to the idle condition. Generally, the process is repeated numerous times as the control unit 160 selects other placements of the anaglyphic image components to cycle through testing conditions.

Typically, a power source (not shown) may be electrically connected to the control unit 160 and/or the anaglyphic image display device 140. As such, the power source assists in supporting operation of some or all of the electrically-driven components. In embodiments, the power source may be a battery, electrical outlet, power cell, solar panel, or any other source of consistent electrical current.

In one instance, an electrical current provided from the power source is controlled by the control unit 160 and conveyed to the plurality of light sources 110 via a communicative connection 162. In another instance, the communicative connection 162 serves to convey a signal from the control unit 160 to the anaglyphic image display device 140 to activate or deactivate one or more selected light sources. Similarly, a communicative connection 164 operably couples the control unit 160 to the input device 170. In this way, the communicative connection 164 allows the input device 170 to convey individual-initiated indications to the control unit 160 and/or control signals from the control unit 160 to the input device 170.

In embodiments, the communicative connections 162 and 164 may be wired or wireless. Examples of particular wired embodiments, within the scope of the present invention, include USB connections and cable connections. Examples of particular wireless embodiments, within the scope of the present invention, include a near-range wireless network and radio-frequency technology. It should be understood and appreciated that the designation of "near-range wireless network" is not meant to be limiting, and should be interpreted broadly to include at least the following technologies: negotiated wireless peripheral (NWP) devices; short-range wireless air interference networks (e.g., wireless personal area network (wPAN), wireless local area network (wLAN), wireless wide area network (wWAN), Bluetooth™, and the like); wireless peer-to-peer communication (e.g., Ultra Wideband); and any protocol that supports wireless communication of data between devices. Additionally, persons familiar with the field of the invention will realize that a near-range wireless network may be practiced by various data-transfer methods (e.g., satellite transmission, telecommunications network, etc.) that are different from the specific illustrated embodiments.

In other embodiments, the anaglyphic image presentation system 100 may not be provisioned with a control unit 160. In this instance, the anaglyphic image display device 140 is wired with switches or relay components incorporated in the wiring to control the routing and timing of the activation of the anaglyphic image display device 140. In this way, when power is applied to the anaglyphic image display device 140, the wiring directs the power to present one or more anaglyphic image components, thereby allowing a user to perceive at least one anaglyphic image.

Generally, the input device 170 is configured to receive response inputs from the individual 130 and to convey the user-input responses to the control unit 160 for processing. By way of example only, individual 130 may input a response after perceiving an anaglyphic image that appears to be the farthest distance from a background panel. Input device 170 may be, for example, a multi-touch device such as an iPod® touch, a microphone, joystick, game pad, wireless device, keyboard, keypad, game controller, force plate, eye tracking system, gesture recognition system, touch sensitive screen, and/or any other input-initiating component that provides wired or wireless data to the anaglyphic image display device 140.

Input device 170 may include voice recognition equipment and/or software that processes auditory inputs from the subject. For example, the auditory input from the subject, in order to show recognition of the visual indicia and/or a visual trait(s) possessed by the visual indicia (for example, if a series of anaglyphic images are presented in a pattern, and the user is asked to input a trait associated with the image possessing the greatest depth), may be a verbalization of the trait possessed by the visual indicia. In one embodiment, if the trait is a directional position of a presented anaglyphic image, the responsive auditory inputs may be "up," "down," "right," and "left." However, one skilled in the art will understand and appreciate that other auditory inputs may be used (e.g., stating a numeral, letter, symbol, etc.) to indicate that the subject perceived and/or recognized the visual indicia. It should be noted, however, that the present invention is not limited to implementation on such input devices 170, but may be implemented on any of a variety of different types of devices within the scope of embodiments hereof. Input indicating the subject's response to a displayed visual indicia may be received and captured with input device 170. If the trait is a directional position, a satisfactory test response may be identifying the quadrant of a display in which an image is located. By way of example only, without limitation, identifying may include the subject providing input by manipulating a joystick in a direction corresponding to the directional orientation on a hand-held device employed as the input device 170.

If input device 170 is a gesture recognition system, a variety of systems and/or methods may be used to receive inputs. For example, one or more cameras may be used to monitor the movement of a subject's body, eyes, limbs and/or extremities and, in conjunction with appropriate hardware and/or software, register an input when subject makes an appropriate gesture. Gesture recognition systems may also utilize optical markers attached to the subject to facilitate motion tracking. Transmitters attached to the subject and receivers (for example, utilizing radio, infrared, sonic, subsonic, or ultrasonic transmissions) may also be utilized as part of a gesture recognition system.

If input device 170 is a touch sensitive screen, any type of touch sensitive screen may be utilized. Also, an overlay of a touch sensitive material may be used to receive touch inputs in conjunction with a display that is not itself touch sensitive. Such an overlay may be any distance from the display.

Although not shown, a recording device may be incorporated within the anaglyphic image presentation system 100. In one instance, the recording device is an external piece of equipment operably coupled to control unit 160 via a communicative connection. In another instance, the recording device is a data-storage component integrated within the control unit 160. In operation, the recording device is configured to retain information such as a record of responses input into the input device 170, a collection of depth perception tests, test instructions, test data, and the like. This information may be searchable at the recording device by the control unit 160 or any other computing device. Further, the information may be downloadable from the recording device to perform analysis thereof, such as calculating a user's history of depth perception measurements or an analysis of improvement in a user's depth perception abilities over time. Further yet, information (e.g., test instructions) may be unloadable to the recording device such that it is accessible to the control unit 160. Although various embodiments of information are discussed above, the content and volume of such information is not intended to limit the scope of embodiments of the present invention in any way.

In embodiments, the control unit 160 may function as a training device by providing feedback to the individual 130. Feedback may be presented in any form and may be based on any information, including depth perception measurements, manipulated test results, and predetermined data from the test instructions. Further, in embodiments, the control unit 160 may function as an analytical processor to evaluate the depth perception abilities of the individual 130. Evaluation may be performed by comparing the response from the individual 130 to the expected response. In one instance, comparing responses comprises comparing the depth perception measurement associated with the user's response to an input device 170 against the depth information that was presented to the user.

In embodiments, the depth perception abilities of a subject may be trained using anaglyphic image presentation system 100 using a series of test parameters as provided below in Table 1. Table 1 comprises a sequence numbering of tests (1, 2, 3, and 4); a prism diopter associated with the perceived anaglyphic image; a prism base direction; an orientation of the colored indicia such as dots displayed on anaglyphic image display device 140; a pix-delta distance between a set of colored dots on anaglyphic image display device 140; and a display time. The prism base direction may be Base-Out (BO), as when the perceived anaglyphic image hovers in front of the background, or Base-In (BI), as when the perceived anaglyphic image hovers behind the background.

As seen below, one exemplary series of training exercises for the anaglyphic image presentation system 100 comprises a series of four tests presented to a subject over the course of two minutes. In embodiments, a subject is presented with a pair of anaglyphic images oriented to hover in front of or behind a background. In embodiments where a user views depth information, such as the anaglyphic images presented, through a set of transmission filter lenses 150 oriented with a red lens covering the right eye and a blue lens covering the left eye, the resulting images with components described in Table 1 will appear to hover in front of behind; in front of and behind the background, respectively.

TABLE 1

| Position | | | Base distance between the | |
|---|---|---|---|---|
| Sequence | Prism Diopter | Prism base direction | Red/Blue dot orientation | center of the dots | Display Time |
| 1 | 1 | BO | BLUE on left RED on right | 173 pixels (4.87 cm) | 30 sec |
| 2 | 1 | BI | RED on left BLUE on right | 173 pixels (4.87 cm) | 30 sec |
| 3 | 2 | BO | BLUE on left RED on right | 345 pixels (9.75 cm) | 30 sec |

TABLE 1-continued

| Position | | | Base distance between the | |
|---|---|---|---|---|
| Sequence | Prism Diopter | Prism base direction | Red/Blue dot orientation | center of the dots | Display Time |
| 4 | 2 | BI | RED on left BLUE on right | 345 pixels (9.75 cm) | 30 sec |

The base distance between the centers of the dots is measured by a pixdelta, as described above. In the present example, the width of one pixel is 0.282 mm. Additionally, the distance between pixels may be referenced by the number of arcseconds associated with each pixdelta. The number of pixels associated with each arcsecond is based on the distance of a subject from a display screen. For instance, when a subject stands sixteen feet from a display screen, a pixdelta of one pixel may comprise twelve arcseconds. Alternatively, when a subject stands thirty two feet from a display screen, a pixdelta of one pixel may comprise six arcseconds. An exemplary table of levels of pixdeltas is shown below.

TABLE 2

| Level | Delta (pixels) | Top Pair distance | Arcseconds |
|---|---|---|---|
| 1 | 10 | Base distance + Delta | 120 |
| 2 | 9 | -OR- | 107 |
| 3 | 8 | Base distance − Delta | 95 |
| 4 | 7 | (Randomly determined) | 84 |
| 5 | 6 | | 72 |
| 6 | 5 | | 60 |
| 7 | 4 | | 48 |
| 8 | 3 | | 36 |
| 9 | 2 | | 24 |
| 10 | 1 | | 12 |

As seen in Table 1 and Table 2, the difference in distance between two pairs of dots presented may be small (e.g., on the order of tenths of millimeters) so as to train the retinal disparity sensitivity aspect of a subject's depth perception ability with substantially unchanged visual vergence. In these cases, a subject's retinal disparity sensitivity would be the primary aspect trained through the anaglyphic image presentation system 100.

In addition to testing the retinal disparity sensitivity aspects of a user's depth perception, the anaglyphic image presentation system 100 may also be used to test and/or train the user's speed in perceiving the distinction between depths presented to the user. The speed of a user's perception may be measured based on the amount of time elapsed from a first time, at which indicia are displayed, and a second time, at which a response is received from the subject. As a user correctly identifies the resulting anaglyphic image that is farthest from the background (or nearest to the background, depending on the test question being asked), the user may be presented with depth information at a faster pace. Additionally or alternatively, the user may be presented with depth information with a smaller pixdelta so as to increase the level of difficulty to the user.

Additionally, although a particular configuration of the anaglyphic image components has been described, it should be understood and appreciated by those of ordinary skill in the art that other methods for presenting the anaglyphic image components could be used, and that the invention is not limited to the embodiments shown and described.

Figure 2:
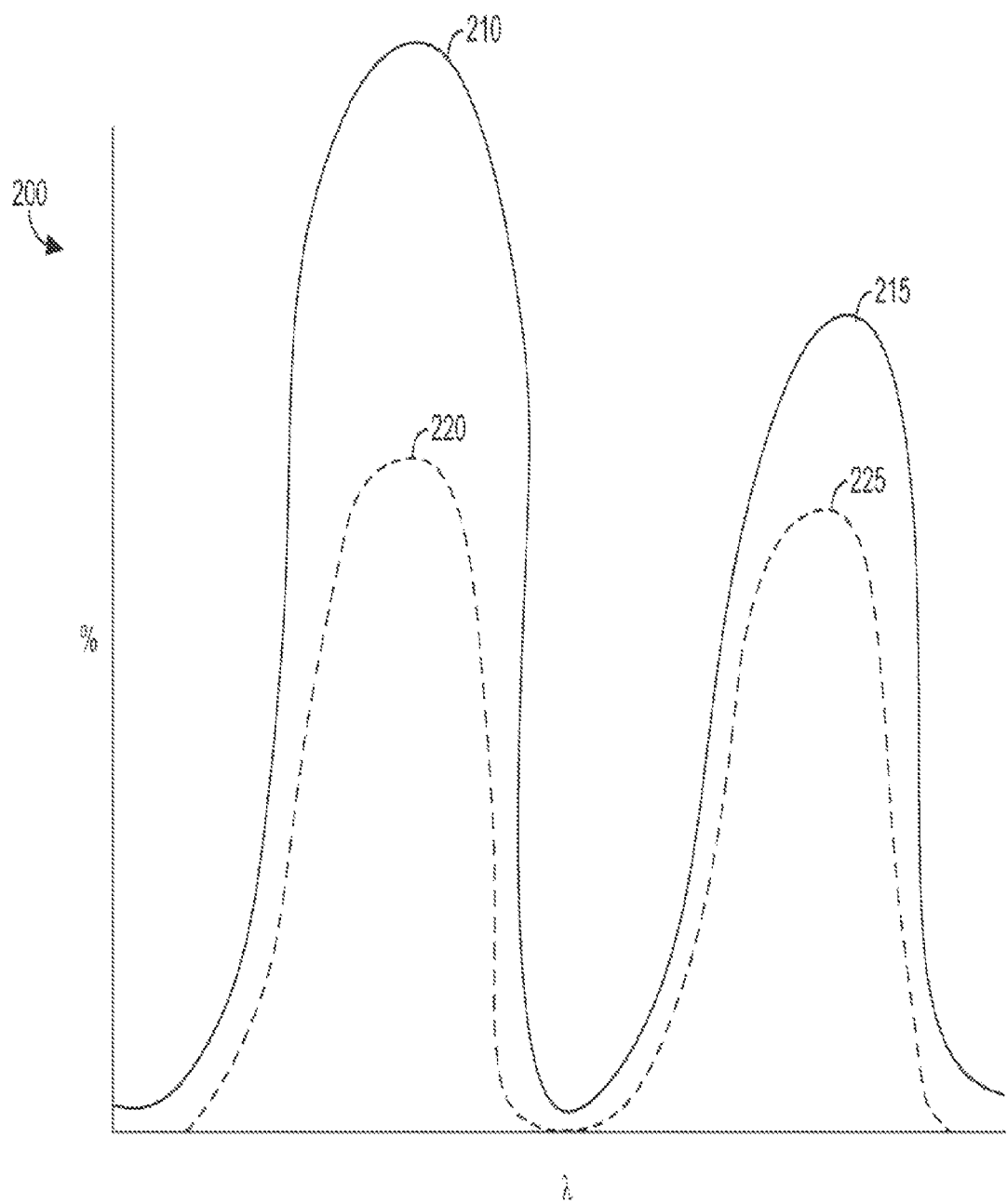
FIG. 2 illustrates an emitted and transmitted wavelength chart plotted against a percentage transmittance of brightness in accordance with an embodiment of the present invention.

Referring to FIG. 2, a transmitted wavelength chart 200 is provided in accordance with an embodiment of the invention.

The chart 200 is composed of measures of percentage transmittance with respect to wavelength on an xy-plot. The chart in FIG. 2 comprises the wavelength and percentage transmittance characteristics of a left target component as displayed 210, a right target component as displayed 215, a left target component as perceived 220, and a right target component as perceived 225.

The wavelength and percentage transmittance of left target component as displayed 210 and right target component as displayed 215 represent the wavelength and percentage transmittance of the components as they would be viewed without filter lenses. Similarly, left target component as perceived 220 and right target component as perceived 225 represent the wavelength and percentage transmittance of the components as they would be viewed through filter lenses. The difference between the two percentages of transmittance at a given wavelength is due to a property of the transmission filter lenses of only letting a percentage of the emitted light pass through the transmission filter lenses. For instance, the light associated with left target component as perceived 220 may only comprise 70% of the light that is displayed, while the light associated with right target component as perceived by 225 may comprise 75% of the light that is displayed. In order to equalize the light that is passed through both sides, the percentage transmittance of the first light must be increased such that the amount of light perceived by a user is equal with regard to the at least two colors being used as anaglyphic input component colors. In alternative embodiments, the percentage transmittance of the background color may be modified to equal the percentage transmittance of the two anaglyphic input components.

Figure 3:
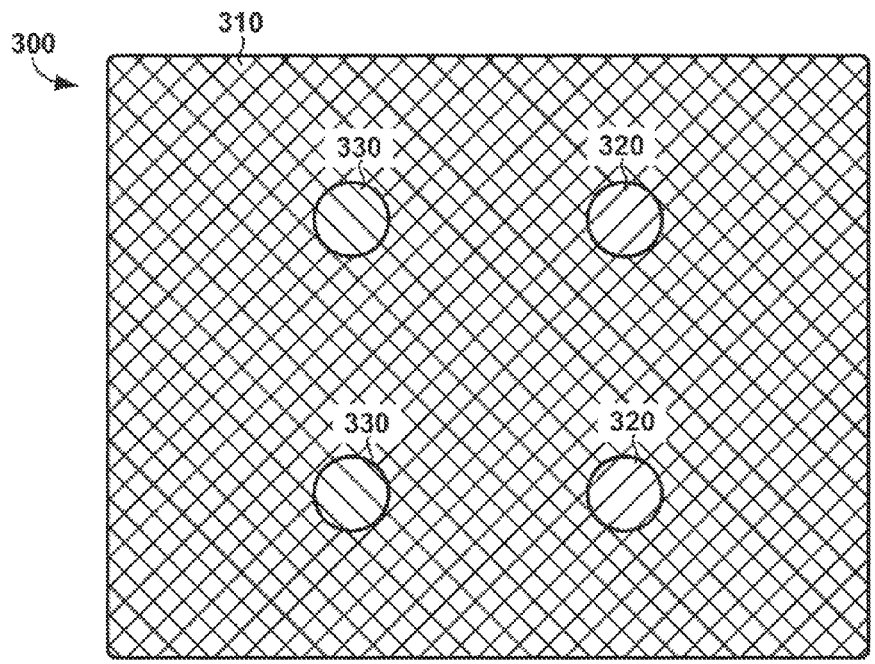
FIG. 3 illustrates an anaglyphic image display device that provides target component images that may be viewed through a set of transmission filter lenses in accordance with an embodiment of the present invention.

FIG. 3 illustrates an anaglyphic image display device 300 that provides target component images that may be viewed through a set of transmission filter lenses in accordance with an embodiment of the present invention. Anaglyphic image display device 300 comprises a background 310, right-oriented anaglyphic image components 320 and left-oriented image components 330. In one embodiment, right-oriented anaglyphic image components 320 are displayed at a first wavelength, such as that associated with red, and left-oriented anaglyphic image components 330 are displayed at a second wavelength, such as that associated with blue. Additionally, background 310 is displayed at a third wavelength that is a mixture of the first wavelength and the second wavelength. Further, the luminance brightness of background 310 and components 320 and 330 are set to be perceived as being equal when perceived through the first and second transmission lenses. For example, background 310 may be displayed at wavelength X and luminance brightness Y; component 320 may be displayed at wavelength X and luminance brightness B; and component 330 may be displayed at wavelength C and luminance brightness D. Thus, in this embodiment, wavelength X will be the chromatic combination of wavelengths A and C, and luminance brightness Y will be the sum of luminance brightnesses B and D.

While the example above uses the colors red and blue for the right-oriented anaglyphic image components and anaglyphic left-oriented image components, respectively, tests have shown that the display of anaglyphic images may be successful using colors that have a lesser degree of luminance contrast than that between blue and red. For instance, in alternative embodiments, shades of green and violet or purple may also be used in composing left-oriented and right-oriented anaglyphic image components.

Figure 4:
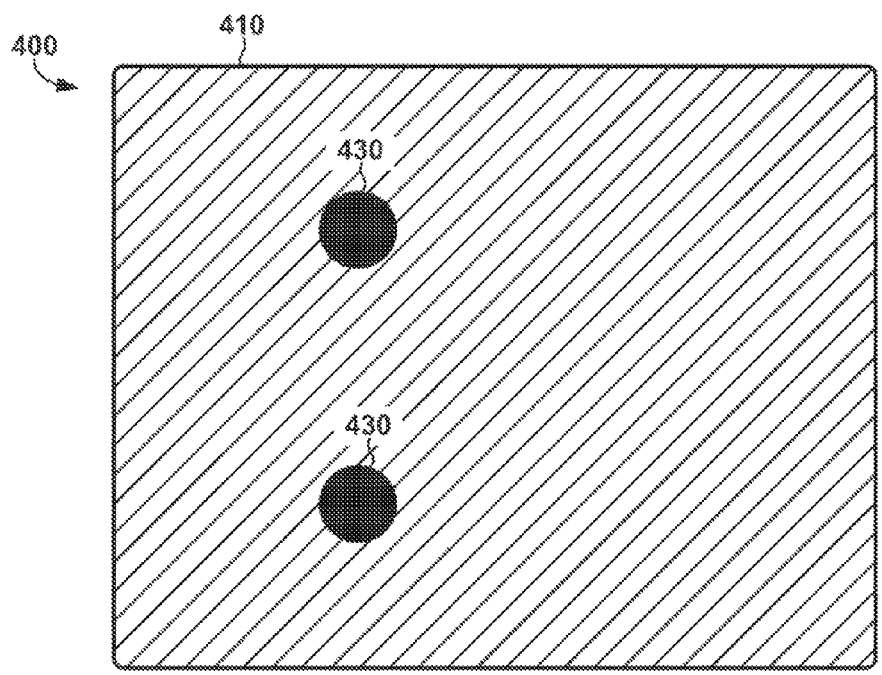
FIG. 4 illustrates a perceived anaglyphic image of an anaglyphic image display device when viewed through a first transmission filter lens in accordance with an embodiment of the present invention.

FIG. 4 illustrates a perceived anaglyphic image 400 of an anaglyphic image display device when viewed through a first transmission filter lens in accordance with an embodiment of the present invention. In this embodiment, the first transmission filter lens is associated with the color red. In particular, an embodiment of the perceived anaglyphic image 400 comprises a background 410 and left-oriented perceived target components 430. Background 410 is displayed at a wavelength associated with the red wavelength and luminance brightness of the peak wavelength transmitted from a first transmission filter lens. As such, the left-oriented perceived target components, which were formally displayed at a wavelength associated with the color blue, now appear to be black. In this embodiment, the left-oriented perceived target components are perceived to be the color black because the color associated with the left-oriented target is completely filtered out by the red filter of the first transmission filter lens. Additionally, the right-oriented anaglyphic image components that were formerly displayed at a wavelength associated with red have now "disappeared" into the resulting purple background when perceived through the first transmission lens. The right-oriented components seem to have disappeared because the color wavelength and luminance brightness at which they were displayed match the wavelength and luminance brightness at which the background 410 is displayed.

Figure 5:
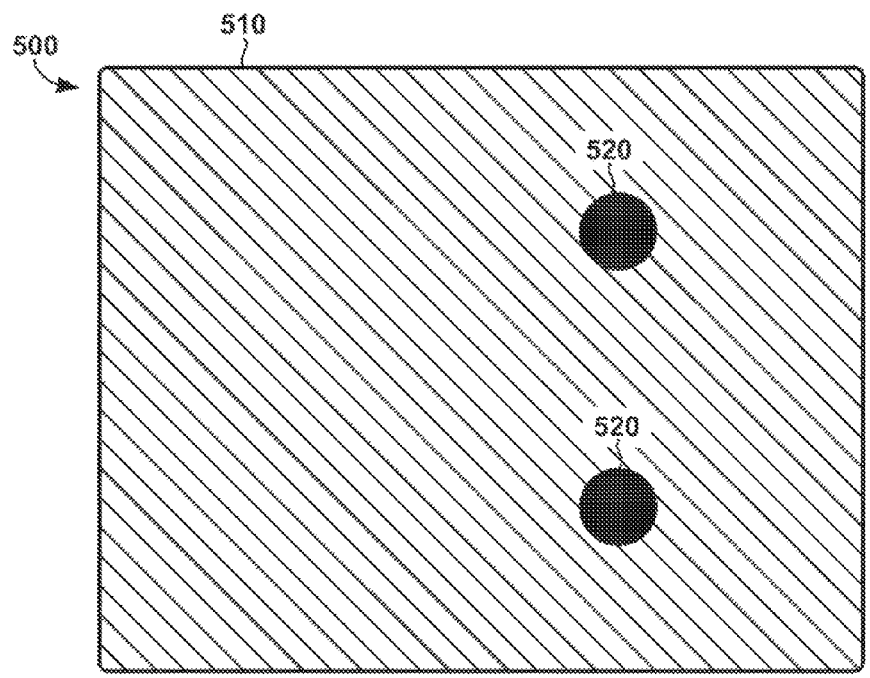
FIG. 5 illustrates a perceived anaglyphic image of an anaglyphic image display device when viewed through a second transmission filter lens in accordance with an embodiment of the present invention.

FIG. 5 illustrates a perceived anaglyphic image 500 of an anaglyphic image display device when viewed through a second transmission filter lens in accordance with an embodiment of the present invention. In this embodiment, the second transmission filter lens is associated with the color blue. In particular, an embodiment of the perceived anaglyphic image 500 comprises a background 510 and right-oriented perceived target components 520. Background 510 is displayed at a wavelength associated with the blue wavelength and luminance brightness of the peak wavelength transmitted from a second transmission filter lens. As such, the right-oriented perceived target components, which were formerly displayed at a wavelength associated with the color red, now appear to be black. In this embodiment, the right-oriented perceived target components are perceived to be the color black because the color associated with the left-oriented target is completely filtered out by the blue filter of the second transmission filter lens. Additionally, the left-oriented anaglyphic image components that were formerly displayed at a wavelength associated with blue have now "disappeared" into the resulting purple background. The left-oriented components seem to have disappeared because the color wavelength and luminance brightness at which they were displayed match the wavelength and luminance brightness at which the background 510 is displayed.

Figure 6:
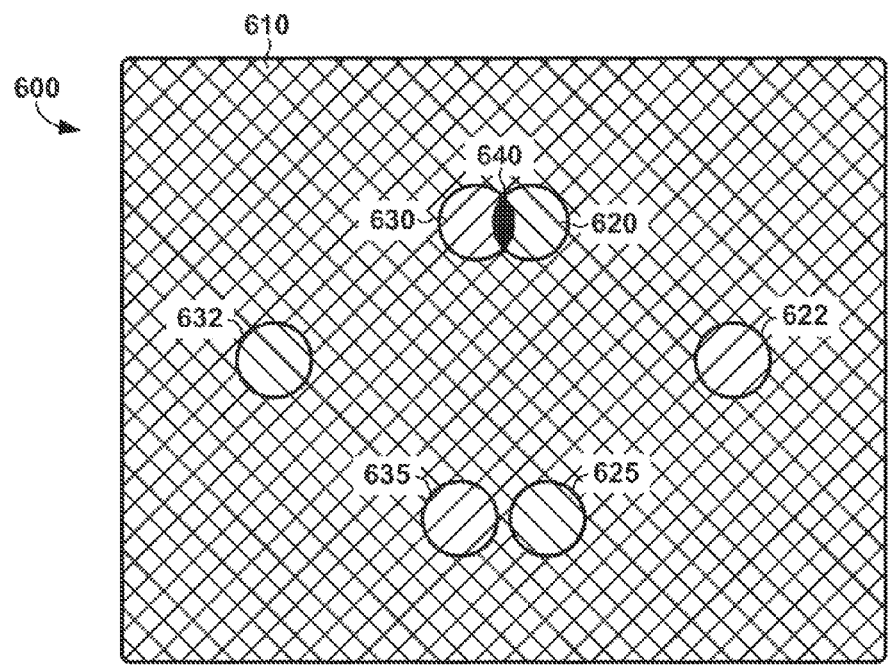
FIG. 6 illustrates a display of anaglyphic image components with various pixdelta displays in accordance with an embodiment of the present invention.

FIG. 6 illustrates a display 600 of anaglyphic image components with various pixdelta displays in accordance with an embodiment of the present invention. The anaglyphic image components are presented against a background 610. There are three sets of pixdelta embodiments: a first set comprising components 620 and 630; a second set comprising components 622 and 632; and a third set comprising components 625 and 635.

Components 620 and 630 are aligned to be consistent with a set of transmission filter lenses with a red lens on the right and a blue lens on the left, such that the first set of components 620 and 630 may be displayed as the colors red on the right and blue on the left, respectively. As such, the resulting anaglyphic image would appear to hover in front of background 610. Similarly, the third set of components 625 and 635 are also consistent with a set of transmission filter lenses, and a resulting anaglyphic image would also appear to be hovering in front of background 610. The distinction between the resulting images from the first set of components 620 and 630 combination and the third set of components 625 and 635 combination is due to the closeness of the components. For instance, the first set of components 620 and 630 are so close as to create a degree of overlap 640, which appears black on display 600 and thus is seen through each filter. The third set of components 625 and 635, however, has no overlap. As such, the anaglyphic image resulting from the third set of components 625 and 635 would appear to be hovering farther in front of background 610 than the resultant anaglyphic image from the first set of components 620 and 630.

In contrast, the second set of components 622 and 632 are inconsistent with a set of transmission filter lenses with a red lens on the right and a blue lens on the left, such that the second set of components 622 and 632 may be displayed as the colors blue on the right and red on the left, respectively. As such, the resulting anaglyphic image would appear to hover behind background 610. Additionally, since the distance between the second set of components 622 and 632 is greater than between either the first set of components 620 and 630 or the third set of components 625 and 635, the image resulting from the second set of components 622 and 632 would appear to have the greatest depth relative to the background 610 (i.e., it would appear to hover the farthest from background 610) of the three resultant anaglyphic images.

Figure 7:
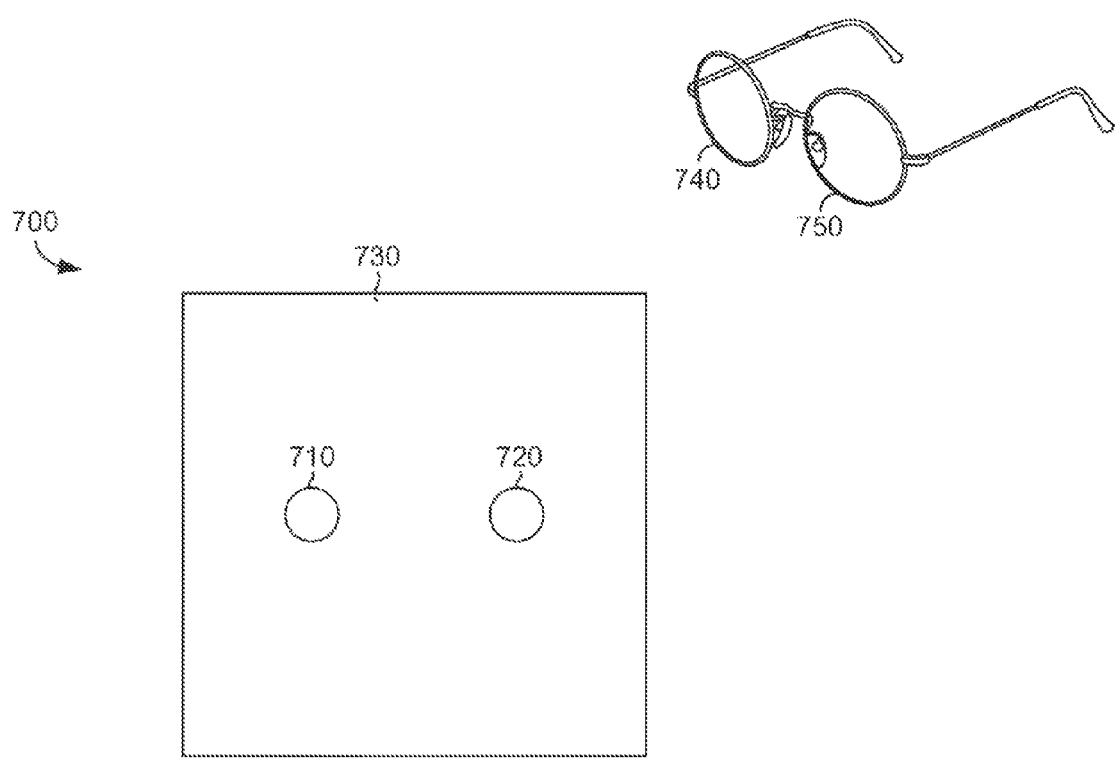
FIG. 7 illustrates an anaglyphic image display device in accordance with an embodiment of the present invention.

FIG. 7 illustrates an anaglyphic image display device 700 in accordance with an embodiment of the present invention. The anaglyphic display device 700 comprises a left-oriented target display component 710, a right-oriented target display component 720, a background 730, a first lens filter 740, and a second lens filter 750. In embodiments, the left-oriented target display component 720 comprises a first color shading at a first wavelength. Similarly, in embodiments, the right-oriented target display component 730 comprises a second color shading at a second wavelength. In further embodiments, the background comprises a third color shading at a third wavelength that comprises a mixture of the first color shading at the first wavelength and the second color shading at the second wavelength. The first lens filter may match the first wavelength. Similarly, the second lens filter may match the second wavelength. Additionally or alternatively, the first lens filter and/or the second lens filter may meet a desired range of wavelengths rather than match a wavelength directly. In alternative embodiments, the luminance contrast between the first color shading at the first wavelength and the third color shading at the third wavelength may be equal to the luminance contrast between the second color shading at the second wavelength and the third color shading at the third wavelength.

Figure 8:
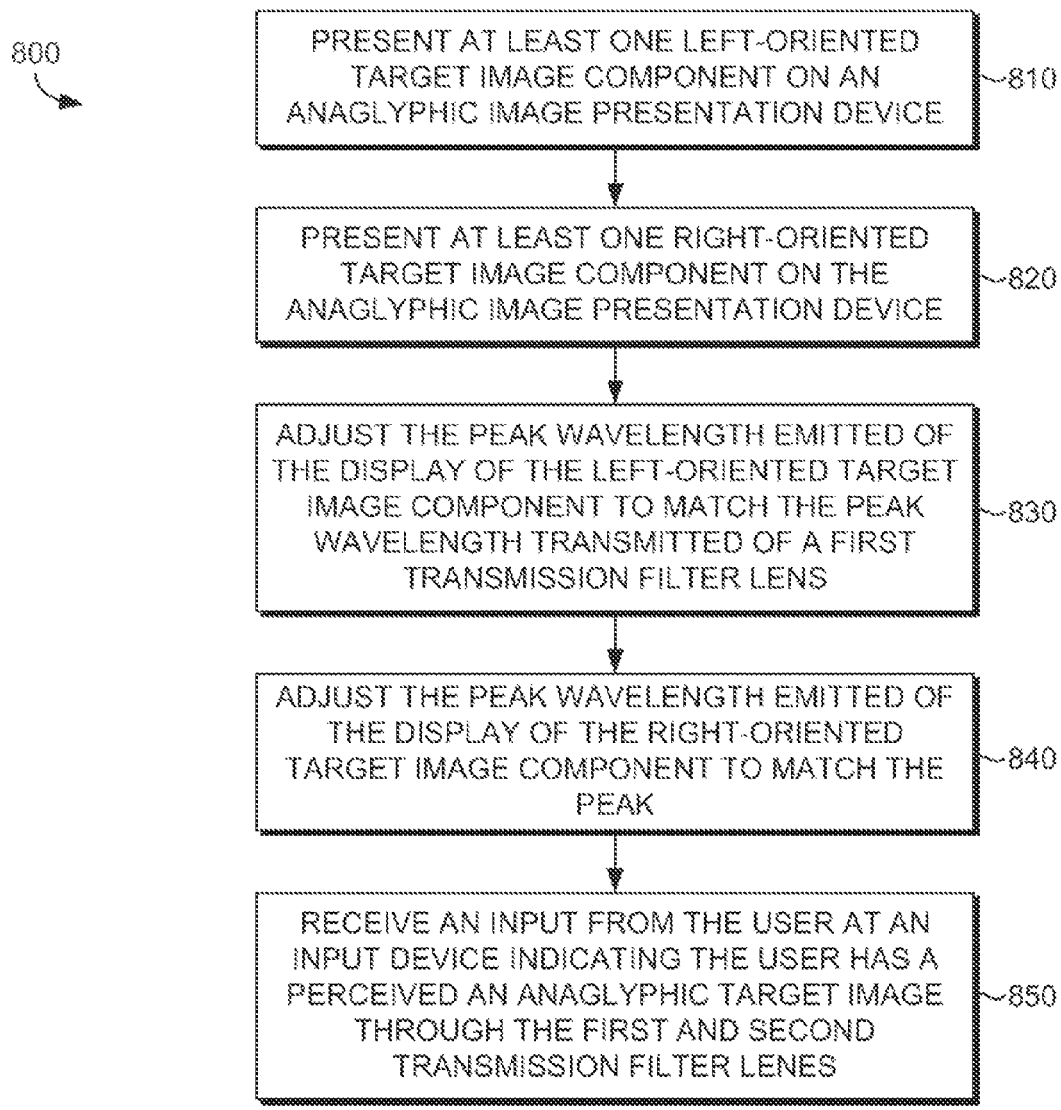
FIG. 8 is a flow diagram showing a method for presenting at least one anaglyphic image to a user in accordance with an embodiment of the present invention.

FIG. 8 is a flow diagram showing a method 800 for presenting at least one anaglyphic image to a user in accordance with an embodiment of the present invention. Initially, at block 810, a left-oriented target image component is presented on an anaglyphic image display device. At block 820, a right-oriented target image component is presented on an anaglyphic image display device. At block 830, the peak wavelength and luminance brightness emitted from the display of the left-oriented target image component is adjusted to match the peak wavelength transmitted by a first transmission filter lens. At block 840, the peak wavelength and luminance brightness emitted from the display of the right-oriented target image component is adjusted to match the peak wavelength transmitted by a second transmission filter lens. At block 850, an input from the user is received at an input device. The input from the user may indicate the user has perceived an anaglyphic target image through the first and second transmission filter lenses. Additionally, the perceived target image may be composed from a compilation of the left-oriented target image component and the right-oriented target image component.

Figure 9:
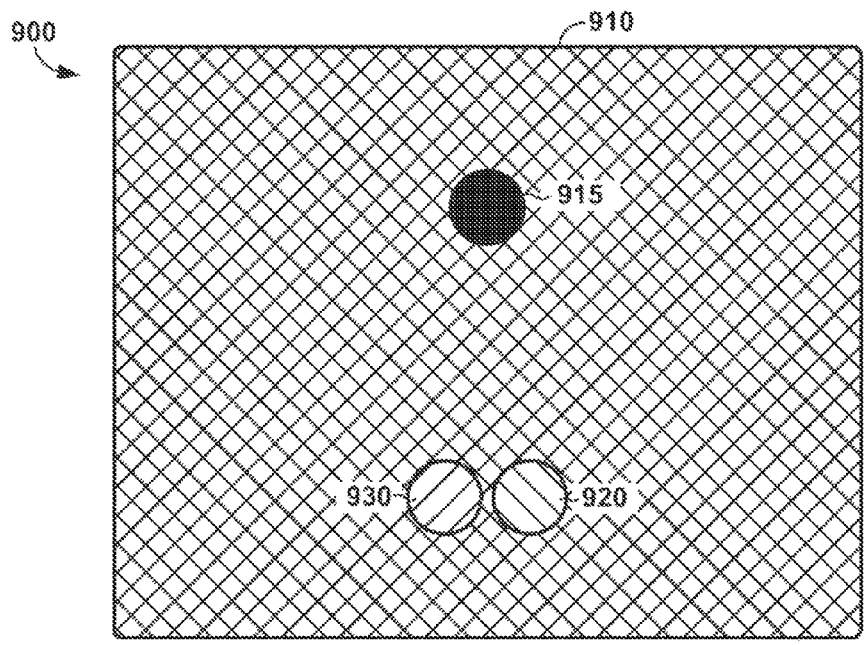
FIG. 9 illustrates a display of anaglyphic image components of a foreground image in relation to a reference image in accordance with an embodiment of the present invention.
Figure 10:
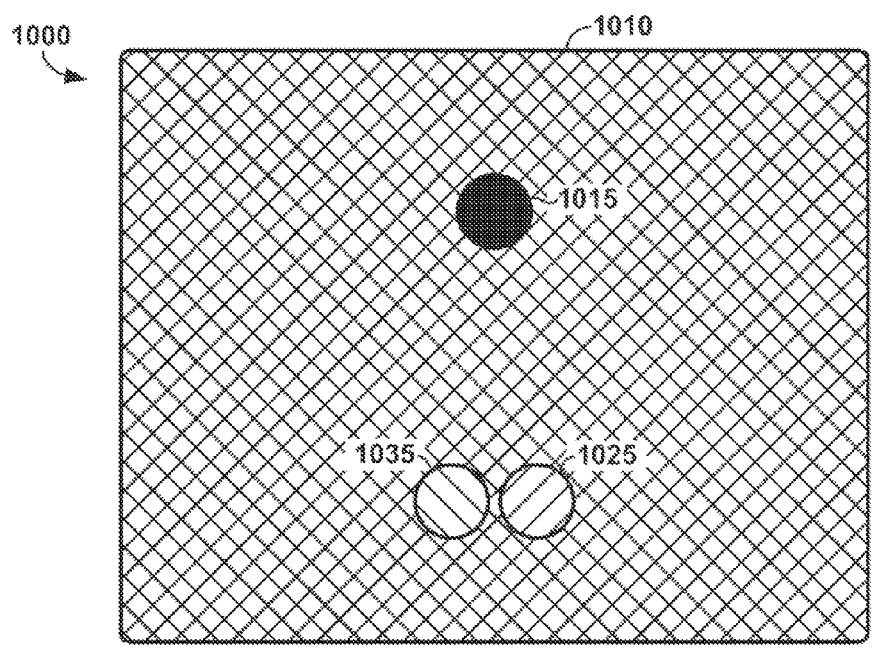
FIG. 10 illustrates a display of anaglyphic image components of a background image in relation to a reference image in accordance with an embodiment of the present invention.
Figure 11:
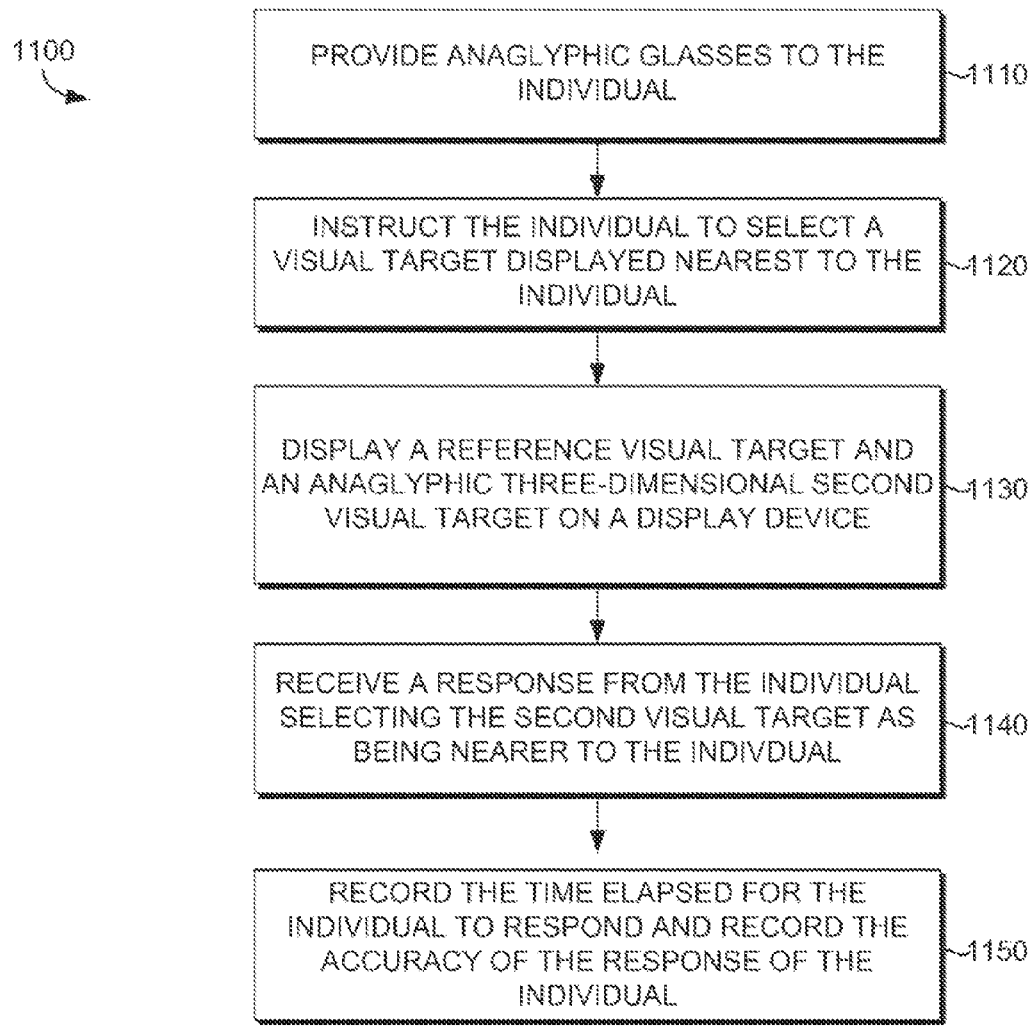
FIG. 11 illustrates a flow diagram showing a further method for presenting at least one anaglyphic image in relation to a reference image to a user in accordance with an embodiment of the present invention.

FIGS. 9-11 illustrate exemplary testing and/or training scenarios in accordance with embodiments of the present invention. In particular, FIGS. 9-11 illustrate the presentation of a reference image and a second image. In embodiments, the reference image is displayed with no anaglyphic effect to appear at the same distance from an individual as a display device. In other words, the reference image occupies a portion of the plane of regard, where the plane of regard is at the surface of a display screen. In embodiments, the second image may utilize anaglyphic effects to appear to hover in front of or behind the reference image to an individual using appropriate eyewear. FIGS. 9 and 10 present alternative testing and/or training scenarios, with FIG. 9 presenting a reference image above a foreground anaglyphic three-dimensional second image. Similarly, FIG. 10 presents a reference image behind a background anaglyphic three-dimensional second image. In testing and/or training scenarios, an individual may be presented with images similar to those seen in FIGS. 9 and 10, with a reference image holding steady at a plane of regard for all testing and/or training iterations while an anaglyphic three-dimensional second image appears to be at different depths in front of and behind reference image 915 and/or 1015, respectively. In alternative embodiments, the presentation of the images may be mutually exclusive, e.g. an individual may be presented one image at a time.

As described above, FIG. 9 illustrates a display 900 of anaglyphic image components of a foreground image in relation to a reference image 915 in accordance with an embodiment of the present invention. In embodiments, a foreground image is an anaglyphic three-dimensional image perceived as being in front of the display device by an individual. Accordingly, components 920 and 930 of the foreground image are aligned to be inconsistent with a set of transmission filter lenses with a red lens on the right and a blue lens on the left, such that the first set of components 920 and 930 may be displayed against background 910 as the colors blue on the right and red on the left, respectively. Further, visual background 910 displays wavelengths matching and cancelling a red peak wavelength transmitted from a first transmission filter lens and a blue peak wavelength transmitted from a second transmission filter lens. FIG. 9 further comprises a reference image 915 that is set within the plane of regard. As such, when visual background 910 is displayed on a surface of a display screen, the reference image 915 appears to be in the plane of the visual background 910. The resulting anaglyphic image appears to hover behind reference image 915 when perceived by an individual through the set of transmission filter lenses as described above. Accordingly, the resulting anaglyphic image is nearer to the individual than reference image 915.

FIG. 10 illustrates a display 1000 of anaglyphic image components of a background image in relation to a reference image 1015 in accordance with an embodiment of the present invention. Accordingly, components 1025 and 1035 of the background image are aligned to be consistent with a set of transmission filter lenses with a red lens on the right and a blue lens on the left, such that the first set of components 1025 and 1035 may be displayed against visual background 1010 as the colors red on the right and blue on the left, respectively. Further, visual background 1010 displays wavelengths matching and cancelling a red peak wavelength transmitted from a first transmission filter lens and a blue peak wavelength transmitted from a second transmission filter lens. FIG. 10 further comprises a reference image 1015 that is set within the plane of regard. As such, when visual background 1010 is displayed on a surface of a display screen, the reference image 1015 appears to be in the plane of the visual background 1010. The resulting anaglyphic image appears to hover in front of reference image 1015 when perceived by an individual through the set of transmission filter lenses as described above. Accordingly, reference image 1015 is nearer to the individual than the resulting anaglyphic image.

FIG. 11 illustrates a flow diagram 1100 showing a further method for presenting at least one anaglyphic image in relation to a reference image to an individual in accordance with an embodiment of the present invention. Initially, at block 1110, anaglyphic glasses are provided to the individual. At block 1120, the individual is instructed to select a visual target displayed nearest to the individual. In alternative embodiments, the individual may be instructed to select a visual target displayed farthest from the individual. In further alternative embodiments, the individual may be instructed to select a visual target within and/or closest to the plane of regard. At block 1130, a reference visual target and an anaglyphic three-dimensional second visual target are displayed on a display device. In particular, the anaglyphic three-dimensional second visual target may be displayed so as to hover in front of the reference visual target when perceived by an individual. In alternative embodiments, block 1130 may occur before block 1120. Further, at block 1140, a response is received from the individual selecting the second visual target as being nearer to the individual than the reference visual target. At block 1150, the time elapsed for the individual to respond is recorded. By recording the time it takes for an individual to record a response to the presented images, the speed of an individual's depth perception may be tested and/or trained. While an individual may be able to discern depths given a sufficient amount of time for his abilities, it may be advantageous for an individual to gain an ability to perceive depths quickly. For example, it may be advantageous for an individual to test and/or train the speed of his depth perception when he is expected to interact in activities involving rapidly changing depths. Additionally at block 1150, the accuracy of the response of the individual is recorded.

In alternative embodiments, an individual may be presented images similar to FIGS. 9 and 10 in order to test and/or train the sensitivity of an individual to foreground and/or background depth perception abilities in relation to a reference image(s) occupying a portion of a plane of regard. For example, an individual may have an above-average ability to discern the depth of a visual image hovering in front of a reference image located at a plane of regard. However, the individual may have a below-average ability to discern the depth of a visual image hovering behind a reference image located at a plane of regard. Accordingly, an individual may be tested and/or trained according to not only his overall visual depth perception, but also according to his abilities to discern between different depths hovering in front of and hovering behind a reference image located at a plane of regard. In alternative embodiments, anaglyphic three-dimensional images in accordance with FIGS. 9 and 10 may be presented at a plurality of discrete depths in front of and/or behind a reference image.

In further alternative embodiments, depth perception abilities of an individual may be tested and/or trained by presenting the individual with anaglyphic images having relatively low vergence demands on the individual. For example, some individuals may have increasing difficulty fusing anaglyphic image components as the distance between the components increases. As such, a testing and/or training regimen may be designed to require a low ability of an individual to fuse anaglyphic image components. In other words, a regimen may be designed to limit the maximum distance between two anaglyphic image components.

Figure 12:
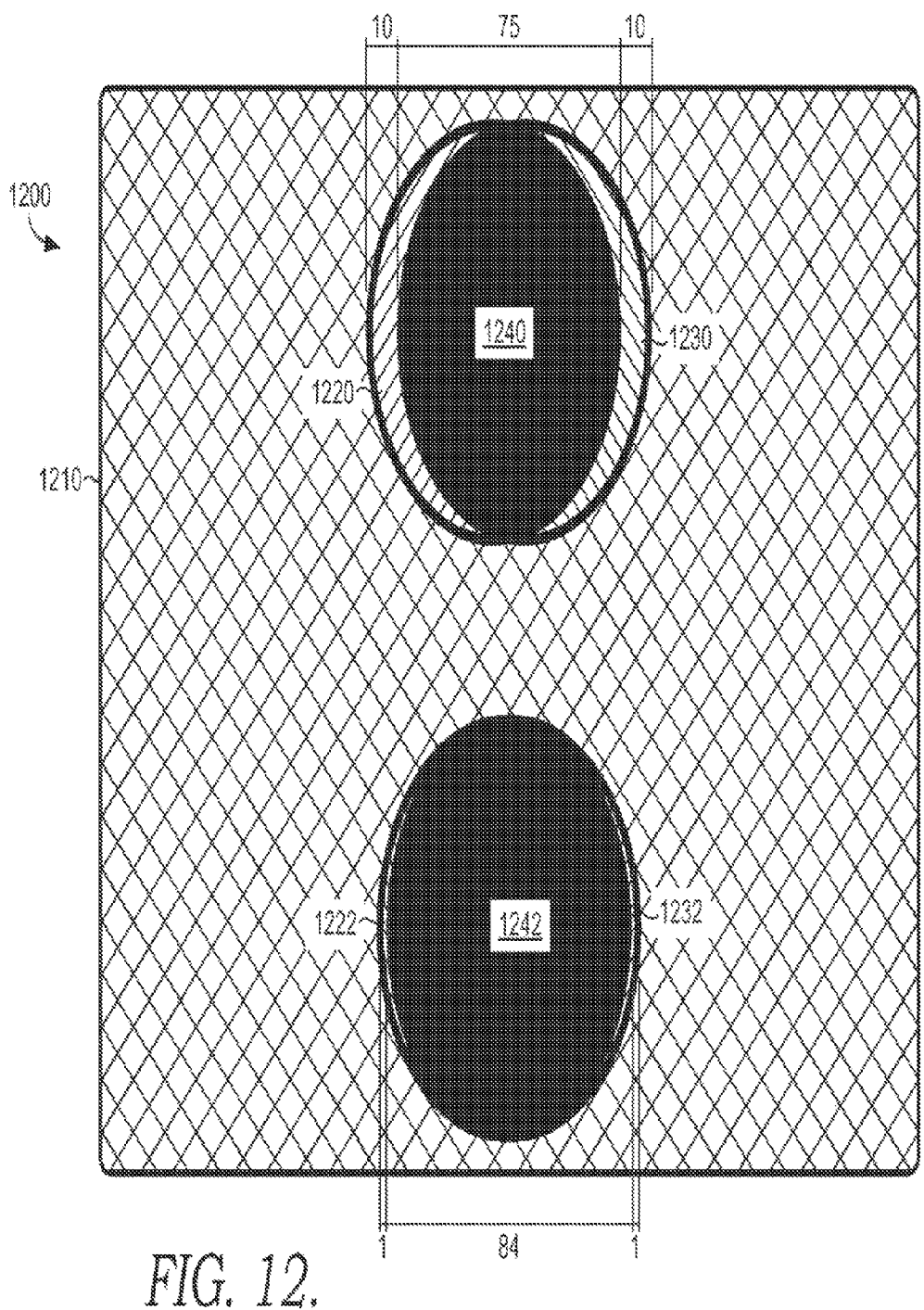
FIG. 12 illustrates image components of two anaglyphic images presented against background in accordance with an embodiment of the present invention.

An embodiment of a regimen for testing and/or training an individual's depth perception abilities may be designed to limit vergence demands on the individual by presenting anaglyphic image components in overlapping configurations. As the anaglyphic image components are overlapping, each anaglyphic image comprising overlapping anaglyphic image components is outside the plane of regard. For example, FIG. 12 illustrates image components 1220, 1222, 1230, and 1232 of two anaglyphic images presented against background 1210 in accordance with an embodiment of the present invention. In embodiments, background 1210 comprises a first wavelength and a second wavelength, where the first wavelength and the second wavelength are equally distributed across the background. In embodiments, portions of the first wavelength may be evenly dispersed with portions of the second wavelength such that the background looks to be one uniform color. For instance, if portions comprising a first wavelength associated with a color blue are equally distributed, for example distributed pixel-by-pixel, with portions comprising a second wavelength associated with a color red, a uniform color of a color purple may result.

A background may comprise a first wavelength and a second wavelength, where the first wavelength and second wavelength are associated with wavelengths of transmission filter lenses and, further, where the first wavelength and second wavelength are associated with wavelengths of anaglyphic image components. When the wavelengths of transmission filter lenses, background colors, and anaglyphic image components are associated, a perceived anaglyphic image may be devoid of a ghost image, such as a crescent-shaped bleed-through effect. The elimination of a crescent-shaped bleed-through effect allows a resulting perceived anaglyphic to be presented with more clarity, which in creases the effectiveness of an anaglyphic system in accordance with the present invention. In contrast, when a first anaglyphic image component and a second anaglyphic image component are presented against a white background, each of a first and a second anaglyphic image component comprising a first wavelength and a second wavelength, respectfully, may display a ghost image, such as a crescent-shaped bleed-through effect, when viewed through transmission filter lenses comprising a second wavelength and a first wavelength, respectively. Since anaglyphic image components are associated with two distinct wavelengths, the ghost image, here a crescent-shaped bleed-through effect, produced when viewing a first anaglyphic image component will not match a ghost image, such as a crescent-shaped bleed-through effect, produced when viewing a second anaglyphic image component, since a characteristic ghost image, such as a crescent-shaped bleed-through effect, is based on the wavelength associated with each image component. Accordingly, when anaglyphic image components are displayed against a white background, an individual may enter responses to perceived anaglyphic images based not only on the individual's perception of depth, but also on the individual's interpretation of perceived ghost image(s) such as crescent-shaped bleed-through effect(s). For instance, an individual may notice that each time an anaglyphic image has a bright ghost image, such as a crescent-shaped bleed-through effect, on a first side and a not-as-bright ghost image, such as a crescent-shaped bleed-through effect, on a second side, that the anaglyphic image has a depth that is coming out towards the user. As such, an individual may be able to input "correct" answers even when he is no longer able to distinguish depth so long as he is able to distinguish ghost image(s), such as crescent-shaped bleed-through effect(s), produced by an anaglyphic testing and/or training process.

By utilizing a background comprising an equal distribution of a first wavelength and a second wavelength, where the first wavelengths and second wavelengths are associated with the transmission filter lenses and anaglyphic image components as described above, ghost image(s), such as crescent-shaped bleed-through effect(s), associated with the anaglyphic image components may be reduced or eliminated. As such, the testing and/or training of an individual's depth perception may be more accurate than if anaglyphic image components used to test and/or train the individual are presented against a white background. In alternative embodiments, non-white backgrounds that do not comprise both the first wavelength and the second wavelength as described above may also be non-ideal. Further, non-white backgrounds comprising the first wavelength, second wavelength, and additional wavelength(s) equally distributed through a background may also be non-ideal. In embodiments, a non-ideal background comprises a background that results in a greater ghost image(s), such as crescent-shaped bleed-through effect(s), than a background comprising a first wavelength and a second wavelength as described in embodiments in accordance with the present invention.

As seen in FIG. 12, components 1220 and 1230 of a first anaglyphic image each have a diameter of 85 units. In embodiments, a unit may comprise a pixel width. Components 1220 and 1230 are aligned to be consistent with a set of transmission filter lenses with a red lens on the right and a blue lens on the left, such that components 1220 and 1230 may be displayed as the colors red on the right and blue on the left, respectively. In embodiments, the wavelength of the blue lens matches the wavelength of the blue anaglyphic image component 1230. Similarly, in embodiments, the wavelength of the red lens matches the wavelength of the red anaglyphic image component 1220. As further seen in FIG. 12, the configuration of components 1220 and 1230 create overlap 1240. Overlap 1240 is black and comprises 75 units of the diameter of each image component 1220 and 1230, leaving a crescent of remaining diameter 10 units of red color and blue color, respectively.

As further seen in FIG. 12, components 1222 and 1232 of a second anaglyphic image each have a diameter of 85 units. In embodiments, a unit may comprise a pixel width. Components 1222 and 1232 are aligned to be inconsistent with a set of transmission filter lenses with a red lens on the right and a blue lens on the left, such that components 1222 and 1232 may be displayed as the colors blue on the right and red on the left, respectively. As further seen in FIG. 12, the configuration of components 1222 and 1232 create overlap 1242. Overlap 1242 is black and comprises 84 units of the diameter of each image component 1222 and 1232, leaving a crescent of remaining diameter 1 unit of blue color and red color, respectively.

In embodiments, an individual standing from sixteen (16) feet from a display device used to present anaglyphic images in accordance with embodiments of the present invention may be tested within a range of 12-240 arcseconds. In embodiments, an individual standing from thirty two (32) feet from a display device used to present anaglyphic images in accordance with embodiments of the present invention may be tested within a range of 6-120 arcseconds. In alternative embodiments, an individual standing from eight (8) feet from a display device used to present anaglyphic images in accordance with embodiments of the present invention may be tested within a range of 24-480 arcseconds. Embodiments such as those described in FIG. 12 may be suitable for individuals who have difficulty fusing image components that are far away from each other. By limiting the demand on an individual's vergence abilities, an individual may be tested and/or trained more accurately based on their sensitivity to depth of presented anaglyphic images. By minimizing vergence between two image components of a perceived anaglyphic image, an individual's depth perception may be more accurately tested and/or trained. Additionally, as discussed above, an individual's speed of recognizing depths may be more accurately tested and/or trained. By recording the time it takes for an individual to record a response to presented anaglyphic images, the speed of the use of an individual's depth perception abilities may be tested and/or trained. While an individual may be able to discern depths given a sufficient amount of time for his abilities, it may be advantageous for an individual to gain an ability to perceive depths quickly. For example, it may be advantageous for an individual to test and/or train the speed of use of his depth perception abilities when he is expected to interact in activities involving rapidly changing depths.

In embodiments, an individual may be presented with two anaglyphic images in accordance with the description above. For example, a first anaglyphic image may be presented in front of a second anaglyphic image. In embodiments, visual components of the first anaglyphic image may be 120 arcseconds apart base out, while visual components of the second anaglyphic image may be 120 arcseconds base in, so that the depth range between the first anaglyphic image and the second anaglyphic image may comprise 240 arcseconds. While a maximum training and/or assessment regimen range of sensitivity training and/or testing may be set at 240 arcseconds, a minimum training and/or testing sensitivity range may be set at 12 arcseconds when viewed by an individual from sixteen (16) feet from a display device in accordance with embodiments of the present invention.

A table of ranges of depth associated with low-vergence embodiments of the present invention is displayed below in Table 3. As seen in Table 3, anaglyphic image components may be presented between +120 arcseconds and −120 arcseconds. Table 3 is based on an individual viewing anaglyphic images on a display device, such as display device 120, from 16 feet away. In accordance with Table 3, an individual may be able to perceive a range of 12-240 arcseconds, when viewed from sixteen (16) feet away, where 12 arcseconds comprises 1 pixel at 0.25 mm width per pixel. As such, the depth perception abilities of an individual may be tested and/or trained to a depth difference of 1 pixel. As such, the minimum testable depth distance of training and/or testing session in accordance with embodiments of the present invention is governed by the resolution of a screen of a display device (such as the size of minimum pixel width) in association with pixel density and the distance of an individual from a display device used in accordance with embodiments of the present invention.

In embodiments, pixel width depends on the type of display(s) used. For instance, in embodiments, an individual viewing anaglyphic images from sixteen (16) feet away on a display having a minimum pixel width of 0.25 mm may be tested and/or trained to a minimum depth difference of 12 arcseconds. In contrast, an individual viewing anaglyphic images from sixteen (16) feet away on an alternative display having a minimum pixel width of 0.5 mm may be tested and/or trained to a minimum depth difference of 24 arcseconds.

In embodiments, an individual may be tested to a minimum depth difference of 12 arcseconds when standing sixteen (16)

feet away when using a Samsung® 120 HZ 3D-Monitor (hereinafter, the "Samsung display"). In embodiments, an individual may be trained through the presentation of anaglyphic images on the Samsung display in accordance with embodiments of the present invention. However, the Samsung display may also be used to test an individual's depth perception through the presentation of alternate images viewed through LCD shutter glasses so as to eliminate a learned effect advantage the individual may have acquired through anaglyphic image training. In embodiments, any display monitor with color capabilities and any resolution may be used in accordance with embodiments of the present invention. An example of an alternative display device comprises a ViewSonic® VX2265wm FuHzion display.

As such, an individual being tested and/or trained in accordance with the range described below only requires the individual to fuse a maximum of 120 arcseconds of depth, either towards the individual or away from the individual. In embodiments, a first anaglyphic image is presented at +120 arcseconds towards the individual while a second image is presented at −120 arcseconds. In this way, an individual may be tested across 240 arcseconds of depth, while the individual being tested may only be required to fuse anaglyphic image components up to 120 arcseconds for any given anaglyphic image.

TABLE 3

| Location | Circle Positions | Intra-distance between circle pair (pixels) | Arc Sec | Appearance on display |
|---|---|---|---|---|
| 1 | RED on right | 10 | +120 | Toward User |
| 2 | Blue on left | 9 | +107 | |
| 3 | (when viewed | 8 | +95 | |
| 4 | through | 7 | +84 | ↑ |
| 5 | transmission | 6 | +72 | |
| 6 | lenses with | 5 | +60 | |
| 7 | Red on right | 4 | +48 | |
| 8 | and | 3 | +36 | |
| 9 | Blue on left, | 2 | +24 | |
| 10 | respectively) | 1 | +12 | |
| 11 | Circles overlap | 0 | 0 | At monitor |
| 12 | BLUE on right | 1 | −12 | |
| 13 | Red on left | 2 | −24 | |
| 14 | (when viewed | 3 | −36 | |
| 15 | through | 4 | −48 | |
| 16 | transmission | 5 | −60 | |
| 17 | lenses with | 6 | −72 | |
| 18 | Red on right | 7 | −84 | ↓ |
| 19 | and | 8 | −95 | Away from user |
| 20 | Blue on left, | 9 | −107 | |
| 21 | respectively) | 10 | −120 | |

Further, a table of exemplary levels associated with low-vergence embodiments of the present invention is displayed below in Table 4. As seen in Table 4, the distance between the two pairs of anaglyphic image component circles is parsed into 20 levels. In embodiments, at level 1, an arcsecond range between a first anaglyphic image and a second anaglyphic image is 240 seconds. In further embodiments, at level 20, an arcsecond range between a first anaglyphic image and a second anaglyphic image is 12 arcseconds. As discussed above, a minimum arcsecond range may depend on a minimum pixel width associated with a display device used to display anaglyphic images to an individual. In alternative embodiments, a designated delta between anaglyphic image component circles may comprise a distance of arcseconds between the anaglyphic image components. For example, at level 1, an associated delta (e.g., pixdelta) of 20 may be representative of 240 arcseconds.

TABLE 4

| Level | Delta (Location difference between the two pairs of circles) | Arcseconds |
|---|---|---|
| 1 | 20 | 240 |
| 2 | 19 | 227 |
| 3 | 18 | 214 |
| 4 | 17 | 202 |
| 5 | 16 | 190 |
| 6 | 15 | 179 |
| 7 | 14 | 168 |
| 8 | 13 | 156 |
| 9 | 12 | 144 |
| 10 | 11 | 132 |
| 11 | 10 | 120 |
| 12 | 9 | 108 |
| 13 | 8 | 96 |
| 14 | 7 | 84 |
| 15 | 6 | 72 |
| 16 | 5 | 60 |
| 17 | 4 | 48 |
| 18 | 3 | 36 |
| 19 | 2 | 24 |
| 20 | 1 | 12 |

The present invention has been described in relation to particular embodiments, which are intended in all respects to be illustrative rather than restrictive. Alternative embodiments will become apparent to those of ordinary skill in the art to which the present invention pertains without departing from its scope.

Figure 13:
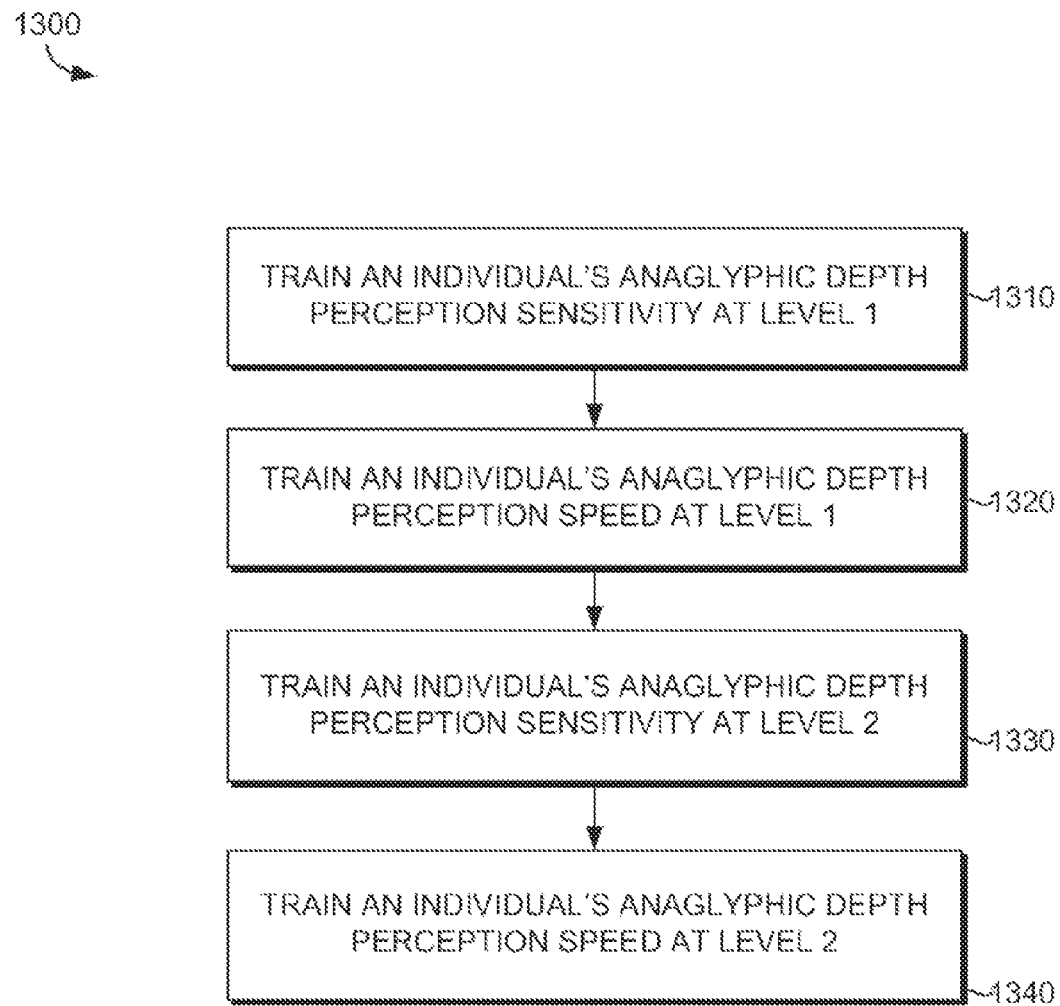
FIG. 13 provides a flow diagram illustrating exemplary training schedules in accordance with embodiments of the present invention.

FIG. 13 provides a flow diagram 1300 illustrating exemplary training schedules in accordance with embodiments of the present invention. In particular, FIG. 13 provides a training regimen wherein an individual's anaglyphic depth perception sensitivity is trained 1310 at a first level, where the first level is associated with a relative measure of arcseconds between two resultant perceived anaglyphic images. Once an individual has mastered training his depth perception sensitivity at a first level, the individual may be trained 1320 in his speed of perceiving differences in depth of images associated with the first level. As discussed above, it may be advantageous for an individual to not only be able to perceive differences in depth, but also to do so quickly. Further, once an individual has mastered training in both sensitivity of depth perception and speed of depth perception associated with a first level, the individual may be trained 1330 on sensitivity of depth perception at a second level. Accordingly, once an individual has mastered his depth perception sensitivity at a second level, the individual may be trained 1340 in his speed of perceiving differences in depth of images associated with the second level.

A further characteristic of testing and/or training an individual's depth perception is provided in FIG. 14. FIG. 14 illustrates a step-training mechanism 1400 in accordance with embodiments of the present invention. In particular, FIG. 14 provides a training regimen wherein an individual being tested and/or trained may be guarded from advancing too quickly based on luck rather than skill. In particular, an individual may be tested and/or trained through the use of a staircase statistical analysis package. An individual being trained using a staircase statistical analysis may be required to correctly identify two depths of anaglyphic images in a row at a first level before proceeding to a subsequent level. Further, once at a subsequent level, the individual may be returned to a lower level if the individual fails one testing and/or training assessment at the subsequent level. In this way, an individual who tries to guess through a training and/or testing assessment will statistically result in low scores, since there is a guessing bias towards being demoted in the training and/or testing assessment.

An exemplary series of results and level adjustments of an individual being tested and/or trained in accordance with embodiments of the present invention is provided in FIG. 14. In particular, an individual may begin his assessment at level 3. In this example, the individual correctly answers a first level three question, and is subsequently given a second level three question since the individual needs to get two answers correct at a first level, in this case level three, before he may advance to a next level. In the example in FIG. 14, the individual then answers his second level three question incorrectly, which results in the individual being demoted to level two. From level two, the individual answers two level two questions correctly, advancing the individual to level three. The individual then answers two level three questions correctly, advancing the individual to level four. The individual then answers a first level four question correctly. In this way, an individual may be tested and/or trained using a plurality of training levels over the course of a series of assessments in accordance with embodiments of the present invention. Further, in alternative embodiments, a testing and/or training assessment may be designed to leave at least a half second pause in between the presentation of assessments so as to avoid perception of images "jumping" forwards and/or backwards between assessments. In this way, individuals may be prevented from gaining an advantage of assessing depths of images relative to assessments the individual(s) has already viewed and/or interpreted.

Figure 15:
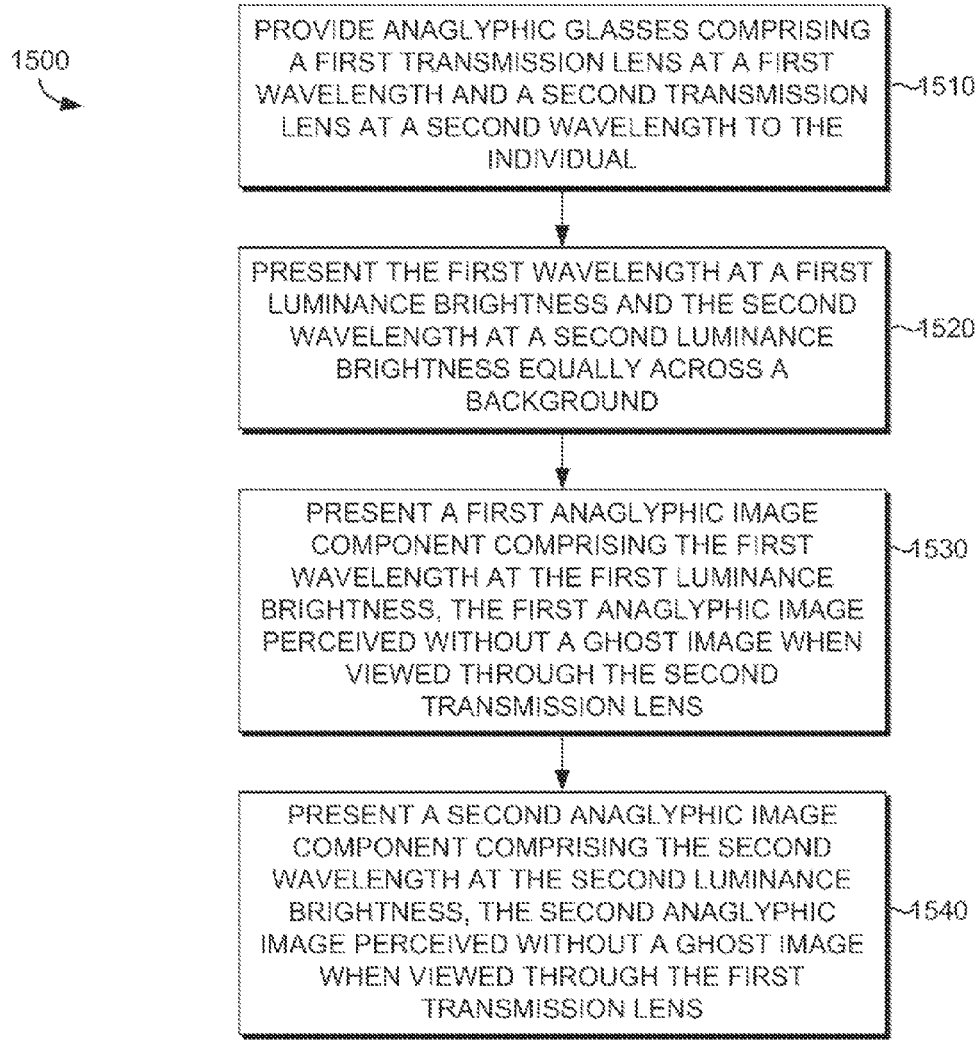
FIG. 15 provides a flow diagram illustrating a method of eliminating a ghost image associated with a presentation of an anaglyphic image in accordance with embodiments of the present invention.

FIG. 15 provides a flow diagram 1500 illustrating a method of eliminating a ghost image associated with a presentation of an anaglyphic image in accordance with embodiments of the present invention. Initially, at block 1510, anaglyphic glasses are provided to an individual. In particular, anaglyphic glasses comprise a first transmission lens at a first wavelength and a second transmission lens at a second wavelength. At block 1520, the first wavelength and the second wavelength are presented across a background. In particular, the first wavelength is presented at a first luminance brightness and the second wavelength is presented at a second luminance brightness. Further, the first wavelength and the second wavelength are distributed equally across the background. At block 1530, a first anaglyphic image component comprising the first wavelength at the first luminance is presented. The first anaglyphic image is perceived without a ghost image when viewed through the second transmission lens. Further, the first anaglyphic image is indistinguishable from the background when viewed through the first transmission lens. At block 1540, a second anaglyphic image component comprising the second wavelength at the second luminance is presented. The second anaglyphic image is perceived without a ghost image when viewed through the first transmission lens. Further, the second anaglyphic image is indistinguishable from the background when viewed through the second transmission lens.

From the foregoing, it will be seen that this invention is one well adapted to attain all the ends and indicia set forth above, together with other advantages which are obvious and inherent to the system and method. It will be understood that certain features and sub-combinations are of utility and may be employed without reference to other features and sub-combinations. This is contemplated by and is within the scope of the claims.

The invention claimed is:

1. An anaglyphic depth perception testing or training device ("anaglyphic device" the anaglyphic device comprising:
   an anaglyphic image display device that presents an anaglyphic background and an anaglyphic image comprised of a first anaglyphic components and a second anaglyphic;
   a first transmission filter lens and a second transmission filter lens, the first transmission filter lens filters a different light wavelength than the second transmission filter lens;
   an input device that receives an input from an individual in response to being presented with the anaglyphic image; and
   a control unit that adjust the anaglyphic background, the first anaglyphic component, or the second anaglyphic component on the anaglyphic image display device in response to the input received at the input device.

2. The anaglyphic device of claim 1, wherein a color of the first anaglyphic component is selected based, in part, on the first transmission filter lens.

3. The anaglyphic device of claim 1, wherein the first transmission filter lens substantially filters a first wavelength, the first wavelength is within a first range of wavelengths.

4. The anaglyphic device of claim 1, wherein the first transmission filter lens and the second transmission filter lens are coupled to a wrap-around eyewear frame.

5. The anaglyphic device of claim 1, wherein a pixdelta between the first anaglyphic component and the second anaglyphic component is adjustable by the control unit.

6. The anaglyphic device of claim 5, wherein the control unit adjusts the pixdelta between the first anaglyphic component and the second anaglyphic component in response to the input received from the input device.

7. The anaglyphic device of claim 1, wherein the anaglyphic image display device presents a second anaglyphic image comprised of a third anaglyphic component and a fourth anaglyphic component.

8. The anaglyphic device of claim 7, wherein the first anaglyphic component and the second anaglyphic component have a different pixdelta than the third anaglyphic component and the fourth anaglyphic component.

9. The anaglyphic device of claim 7, wherein the first anaglyphic component and the third anaglyphic component are displayed on the anaglyphic image display device as using a first coloration and the second anaglyphic component and the fourth anaglyphic component are displayed on the anaglyphic image display device as using a second coloration.

10. The anaglyphic device of claim 7, wherein the first anaglyphic image appears at a different depth than the second anaglyphic image.

11. A method for presenting at least one anaglyphic image to a user, the method comprising:
    presenting a first image component on an anaglyphic image display device;
    presenting a second image component on the anaglyphic image display device, wherein the first image component and the second image component form a first anaglyphic image;
    adjusting a peak wavelength emitted from the display with respect to the first image component to coordinate with a first peak wavelength transmission range of a first transmission filter lens;
    adjusting a peak wavelength emitted from the display with respect to the second image component to coordinate with a second peak wavelength transmission range of a second transmission filter lens, wherein the first peak wavelength transmission range and the second peak wavelength transmission range are different peak wavelength transmission ranges; and receiving an input from a user indicating the user perceived the anaglyphic image through the first transmission filter lens and the second transmission filter lens.

12. The method of claim 11, wherein the first transmission filter lens coordinates with the first wavelength when a peak wavelength transmitted through the first transmission filter lens is within a first range of appropriate wavelengths.

13. The anaglyphic image presentation system of claim 12, wherein the second transmission filter lens coordinates with the second wavelength when a peak wavelength transmitted through the second transmission filter lens is within a second range of appropriate wavelengths.

14. The anaglyphic image presentation system of claim 11, wherein the first transmission filter lens coordinates with the first wavelength when a peak wavelength transmitted through the first transmission filter lens is within a farther 50% range of a first range of appropriate wavelengths when compared to the second range of appropriate wavelengths.

15. The anaglyphic image presentation system of claim 14, wherein the second transmission filter lens coordinates with the second wavelength when a peak wavelength transmitted through the second transmission filter lens is within a farther 50% range of a second range of appropriate wavelengths when compared to the first range of appropriate wavelengths.

16. The anaglyphic image presentation system of claim 11, wherein the first and second transmission filter lenses are coupled with an eyewear frame useable by the user.

17. A method for presenting at least one anaglyphic image to a user, the method comprising:
presenting a first image component on an anaglyphic image display device;
presenting a second image component on the anaglyphic image display device, wherein the first image component and the second image component form a first anaglyphic image;
presenting a third image component on the anaglyphic image display device;
presenting a fourth image component on the anaglyphic image display device, wherein the third image component and the fourth image component form a second anaglyphic image;
adjusting a peak wavelength emitted from the display with respect to the first image component and the third image component to coordinate with a first peak wavelength transmission range of a first transmission filter lens;
adjusting a peak wavelength emitted from the display with respect to the second image component and the fourth image component to coordinate with a second peak wavelength transmission range of a second transmission filter lens, wherein the first peak wavelength transmission range and the second peak wavelength transmission range are different peak wavelength transmission ranges; and
receiving an input from a user indicating the user perceived, through the first transmission filter lens and the second transmission filter lens, the first anaglyphic image as having a greater depth than the second anaglyphic image.

18. The method of claim 17 further comprising:
in response to receiving the input, adjusting a pixdelta between the first image component and the second image component.

19. The method of claim 17 further comprising:
ceasing to present the first image component and the second image component after a predetermined time.

20. The method of claim 19 further comprising:
adjusting the predetermined time in response to the input.

* * * * *